United States Patent [19]
Budgifvars et al.

[11] Patent Number: 5,709,225
[45] Date of Patent: Jan. 20, 1998

[54] COMBINED MAGNETIC FIELD DETECTOR AND ACTIVITY DETECTOR EMPLOYING A CAPACITIVE SENSOR, FOR A MEDICAL IMPLANT

[75] Inventors: Göran Budgifvars; Inga Bergström, both of Stockholm, Sweden

[73] Assignee: Pacesetter AB, Solna, Sweden

[21] Appl. No.: 531,274

[22] Filed: Sep. 20, 1995

[30] Foreign Application Priority Data

Sep. 22, 1994 [SE] Sweden ............... 9403188

[51] Int. Cl.⁶ .................. A61B 5/11; A61N 1/365
[52] U.S. Cl. .................. 128/899; 607/17; 607/32; 128/903
[58] Field of Search ............... 607/27–32, 17; 128/899, 903

[56] References Cited

U.S. PATENT DOCUMENTS

| | | |
|---|---|---|
| 4,140,132 | 2/1979 | Dahl . |
| 4,541,431 | 9/1985 | Ibrahim et al. . |
| 4,884,575 | 12/1989 | Sanders . |
| 5,309,096 | 5/1994 | Hoegnelid ............... 607/17 |
| 5,425,750 | 6/1995 | Moberg ............... 607/17 |
| 5,545,187 | 8/1996 | Bergström et al. ............... 607/32 |

FOREIGN PATENT DOCUMENTS

| | | |
|---|---|---|
| 0 530 006 | 3/1993 | European Pat. Off. . |
| 0 538 899 | 4/1993 | European Pat. Off. . |
| 0 590 178 | 4/1994 | European Pat. Off. . |

*Primary Examiner*—Jeffrey R. Jastrzab
*Attorney, Agent, or Firm*—Hill, Steadman & Simpson

[57] ABSTRACT

A medical implant contains a magnetic field detector with a sensor whose capacitance changes in the presence of a magnetic field with a predefined strength, and a capacitance-controlled unit connected to the sensor. The capacitance-controlled unit sends a measurement signal to a detection unit. If a measurement signal parameter affected by capacitance exhibits a specific change over a predefined period of time, a detection signal is generated by the detection unit to indicate the presence of a magnetic field. The sensor's capacitance also changes when the sensor moves, and this is utilized for measuring activity in an activity measurement circuit connected to the capacitance-controlled unit and for generating an activity signal on the basis of the measurement signal.

6 Claims, 3 Drawing Sheets

5,709,225

COMBINED MAGNETIC FIELD DETECTOR AND ACTIVITY DETECTOR EMPLOYING A CAPACITIVE SENSOR, FOR A MEDICAL IMPLANT

BACKGROUND OF THE INVENTION

1. Field of the Invention

The present invention relates to a medical implant containing a magnetic field detector and an activity detector.

2. Description of the Prior Art

In a medical implant such as a pacemaker, a magnetic field detector is used for non-invasive activation of different implant functions by means of, e.g., a permanent magnet which is moved adjacent to the implant on the exterior of the patient's body. With a pacemaker, for example, some of the functions which can be activated are disabling the pacemaker's demand function so the pacemaker adapts its operation to the battery's capacity, having the pacemaker operate according to some special temporary stimulation mode (e.g. in tachycardia) and programming the pacemaker.

Detection of magnetic fields in the context of devices other than implants is accomplished in a number of different known ways, e.g., with the aid of reed switches or by changing the resonance frequency or inductance etc.

In the implant art, a conventional magnetic field detector consists of a reed switch. A reed switch, however, is a sensitive and rather expensive component which also occupies a relatively large amount of space in the implant.

In order to eliminate the need for reed switches, utilization of the implant's telemetry unit for detecting the presence of magnetic fields, in addition to providing telemetric functions, has been proposed in recent years.

U.S. Pat. No. 4,541,431 discloses one such proposal with a combined telemetry and magnetic field detector unit. The detector disclosed therein contains a conventional resonant circuit, with e.g., a coil, employed in telemetry for transmitting and receiving data. The resonant circuit is also used for sensing the presence of magnetic fields whose strength exceeds a predefined value. The resonant frequency of the resonant circuit varies with the strength of the magnetic field. The resonant circuit is activated periodically, and the number of zero crossings of the output signal of the resonant circuit are analyzed during a sensing window having a defined duration. If a given number of zero crossings occurs in the sensing window, this means that the strength of the magnetic field exceeds the predefined valued.

Most contemporary pacemakers have some form of sensor-activated control of the pacemaker's stimulation rate and often use an activity sensor. One example of such a sensor-controlled pacemaker is disclosed in U.S. Pat. No. 4,140,132 which contains a sensor, e.g. a piezoelectric element, which changes the pacemaker's stimulation rate on the basis of the vibrations of the piezoelectric element.

SUMMARY OF THE INVENTION

An object of the present invention is to provide an improved device for detecting magnetic fields near an implant which can also detect activity of the patient in whom the implant is implanted.

The above object is achieved in accordance with the principles of the present invention in a medical implant having a magnetic field detector, the magnetic field detector containing a capacitive sensor which is at least partially coated with a material that is sensitive to magnetic fields, the coating of material causing a change in the capacitance of the sensor in the presence of a magnetic field. The change in capacitance causes the sensor to generate a detection signal when a magnetic field having a predetermined field strength is present. The capacitor also has a plate which moves dependent on activity of the patient, thereby producing a capacitance change due to activity. A capacitance-controlled amplifier is connected to the sensor, this amplifier emitting a measurement signal, with gain then being the measurement signal parameter affected by capacitance. According to this first preferred embodiment, the magnetic field detector is also employed for activity measurement.

According to the invention, therefore, the need for a reed switch as a magnetic field detector is eliminated by instead using a capacitive sensor already in the pacemaker. At least part of the sensor is coated with a material, sensitive to magnetic fields, which causes a change in the sensor's capacitance in the presence of a magnetic field, a detection signal thereupon being generated on the basis of this change in capacitance in the presence of the magnetic field.

According to one embodiment, a capacitance-controlled amplifier is connected connected to the sensor, this oscillator emitting a measurement signal, with frequency then being the measurement signal parameter affected by capacitance. According to this second embodiment, the magnetic field detector is also employed for activity measurement.

According to third and fourth embodiments, the measurement signal parameters affected by capacitance are gain and frequency respectively, exactly as in the first two embodiments. The difference between these embodiments and the first two is that there is no activity measurement in the third and fourth embodiments.

The sensor used is a capacitive accelerometer containing at least two electrode plates, moveable in relation to each other, at least one of the electrode plates being coated with a material sensitive to magnetic fields, e.g. a ferromagnetic material or a permanent magnet material, whereby the sensor's capacitance depends on the distance between the electrode plates.

DESCRIPTION OF THE PREFERRED EMBODIMENTS

Figure 1:
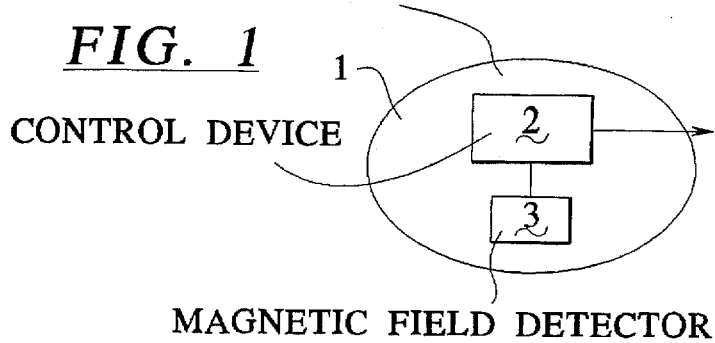
FIG. 1 is a schematic block diagram of a medical implant including a magnetic field detector constructed in accordance with the principles of the present invention.

Identical or similar parts in the drawings have the same reference designations.

FIG. 1 shows a medical implant 1 containing a control device 2 to which a magnetic field detector 3 is connected. The implant 1 can be a pacemaker, a defibrillator, a nerve stimulator or some other implantable device. Accordingly, the implant 1 contains a therapy generating device 16, such as a pacing pulse and/or defibrillation pulse generator, and a therapy delivery device 17, such as an implantable cable with pacing and/or defibrillation electrodes. The therapy generating device 16 is controlled by the control unit 2 to change the therapy mode, such as changing a pacing mode, in the presence of a detected magnetic field, and to adjust the therapy, such as by changing the pacing rage, dependent on patient activity.

Figure 2:
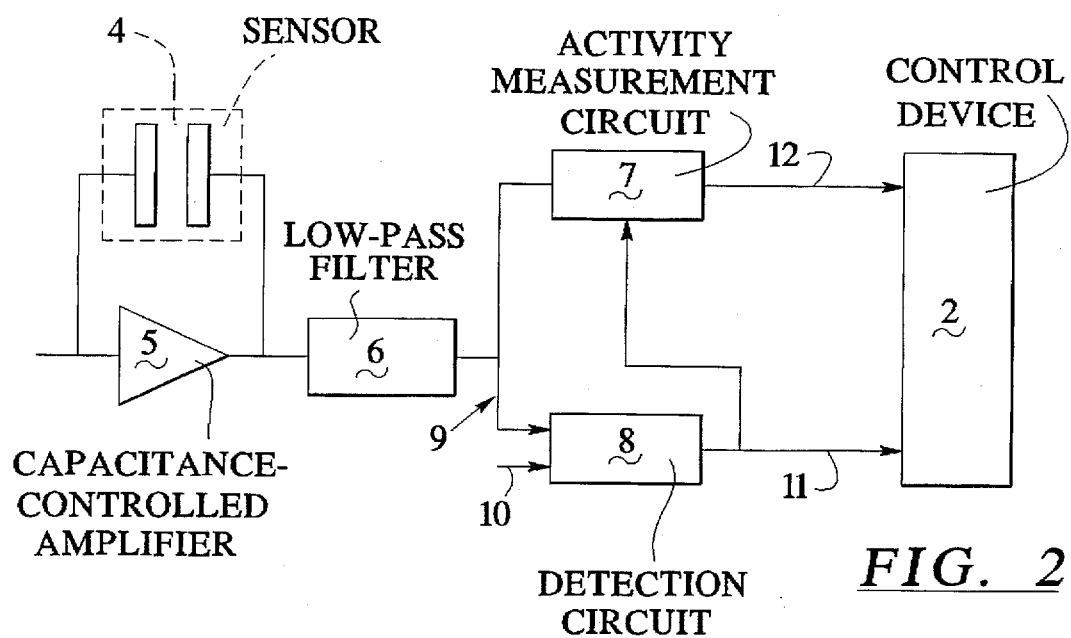
FIG. 2 is a schematic block diagram of a first embodiment of a magnetic field/activity detector according to the invention.

FIG. 2 shows the magnetic field detector 3 according to a first embodiment, the magnetic field detector 3 containing a capacitive sensor 4, a capacitance-controlled amplifier 5, a low-pass filter 6, an activity measurement circuit 7 and a detection unit 8.

The sensor 4 is a capacitive accelerometer containing at least two electrode plates, a mass element being attached to one of the plates. When the sensor moves, the plate with the mass element moves toward or away from the other plate, causing a change in the sensor's capacitance. If the plate with the mass element is coated with a material sensitive to magnetic fields, such as a ferromagnetic material or a permanent magnet material, the presence of a magnetic field will change the distance between the plates, thereby changing the capacitance of the sensor 4. The capacitance change caused by the presence of a magnetic field is much greater than the change induced by acceleration due to physical activity. The magnitude of the change in capacitance depends on the thickness of the material, sensitive to magnetic fields, with which the electrode plate is coated and can be established during the fabrication of the sensor 4.

In order to achieve a magnetic field with a defined strength, an ordinary permanent magnet, placed on the patient's skin above the implant, is used. A requirement for a modern pacemaker is that the pacemaker must be able to detect a magnet at a distance of 40 cm.

The sensor 4 is connected to the amplifier 5 in such a way that the capacitance of the sensor affects the gain of the amplifier 5. The amplifier 5 has a direct current voltage input signal. The output signal of the amplifier 5 is filtered in the low-pass filter 6, thereby producing a measurement signal 9. The measurement signal 9 is supplied to the activity measurement circuit 7 and the detection circuit 8. The measurement signal 9 is compared in the detection circuit 8 to an adjustable voltage threshold value 10. If the measurement signal 9 exceeds this threshold value 10 for a predefined period of time, a detection signal 11 is generated and sent to the control device 2. The voltage threshold 10 is set at a value corresponding to a measurement signal level when a magnetic field with a predefined strength is present. The detection signal 11 is sent to the control device 2 and also is used as a control signal for the activity measurement circuit 7. The activity measurement circuit 7 sends an activity signal 12 to the control device 2 when no detection signal 11 is sent to the activity circuit 7. The activity signal 12 is used in the control device 2 for, e.g., changing the pacemaker's stimulation rate.

In order to prevent transient increases in the magnetic field from causing erroneous detection of a magnetic field, two conditions must be met for the detection signal 11 to be generated. Firstly, the measurement signal 9 must exceed the voltage threshold value 10. Secondly, the measurement signal 9 must exceed the threshold value 10 for a predefined period of time. A detection signal 11 is only generated if these two conditions are met.

The detection circuit 8 also includes a time measuring circuit (not shown), in addition to a voltage comparison circuit (not shown), for determining whether the measurement signal 9 exceeds the threshold value 10 for the predefined period of time. The voltage comparison circuit and the time measurement circuit will not be described here, since they are components familiar to those skilled in the art.

The duration of the predefined interval is selected at the time the implant is programmed and set at a value about the same as a normal stimulation interval (857 ms). A normal stimulation interval of 857 ms corresponds to a stimulation rate of 70 beats a minute. The interval is set at a value of this magnitude because it is assumed that any movement-induced change in capacitance cannot remain constant that long, thereby preventing movement from being erroneously interpreted as the presence of a magnetic field.

If a detection signal 11 is sent to the control device 2, the control device 2 performs the aforementioned activities to be carried out when the implant is in the magnet mode. These will not be described here, since they are measures familiar to those skilled in the art.

If no magnetic field is detected, the control device 2 exits from the magnet mode, and the activity measurement circuit 7 is reactivated.

Figure 3:
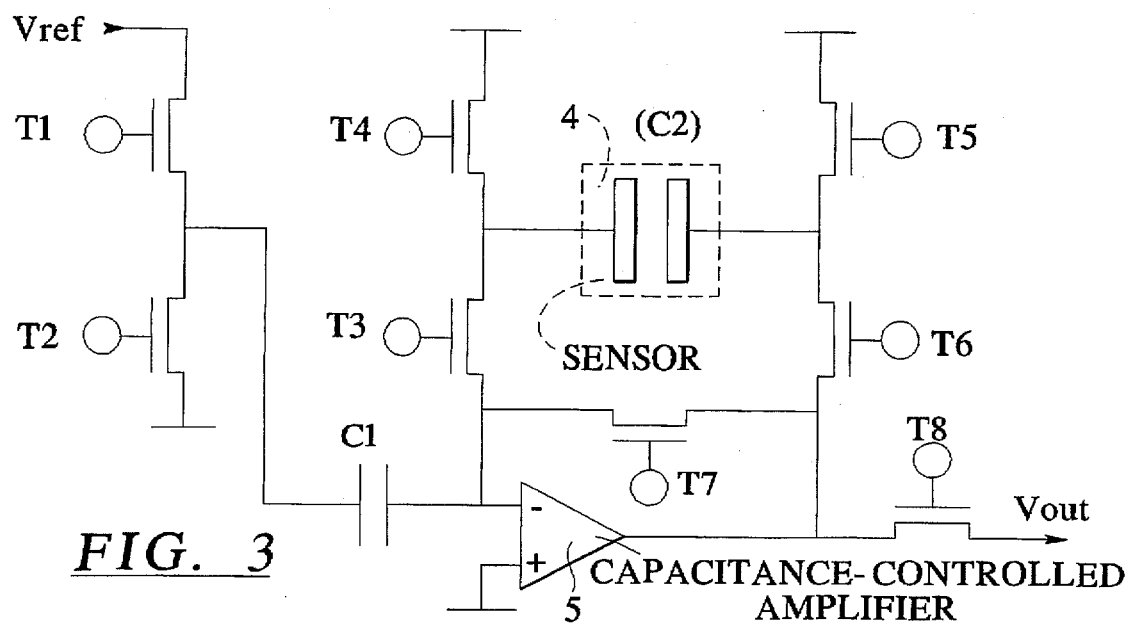
FIG. 3 is a detailed circuit diagram of the capacitance-controlled amplifier according to the first embodiment.

FIG. 3 is a more detailed circuit diagram showing the circuitry of the capacitance-controlled amplifier 5. The circuit contains eight switching transistors, T1–T8, and a switching capacitor, C1. The capacitance of the sensor 4 is designated C2. Vref designates a direct current voltage constituting an appropriate fraction of the implant's battery voltage. The transistors T1–T8 serve as switches and are controlled by the control device 2 with a digital clock (not shown) created by reduction of the frequency of a crystal oscillator (not shown). The switching rate selected depends on the circuit design, but a frequency on the order of 500 Hz is selected. The transistors are switched in groups in which the transistors in an initial group, T1, T4, T5 and T7, are conducting simultaneously and in which the transistors in a second group, T2, T3 and T6, are non-conducting. The groups are enabled alternatively, and the amplifier's output voltage, $V_{out}$, only supplies a measurement value when the second group is enabled and conducting. The output voltage $V_{out}$ is sampled with T8 which is enabled at the same time as the second group. The described activation of the amplifier 5 is a type referred to as "switched-capacitor" (SC) arrangement. Switching is based on the fact that when a capacitor is alternatively charged and discharged, a resistance is simulated which can approximately be calculated as $R=1/(f_s \cdot C)$, in which $f_s$ is the clock rate. The output voltage $V_{out}$ from the amplifier 5 can now be written as $V_{out}=(1/(f_s \cdot C2)/1/(f_s \cdot C1)) \cdot Vref$, yielding through consolidation $V_{out}= (C1/C2) \cdot Vref$.

Figure 4:
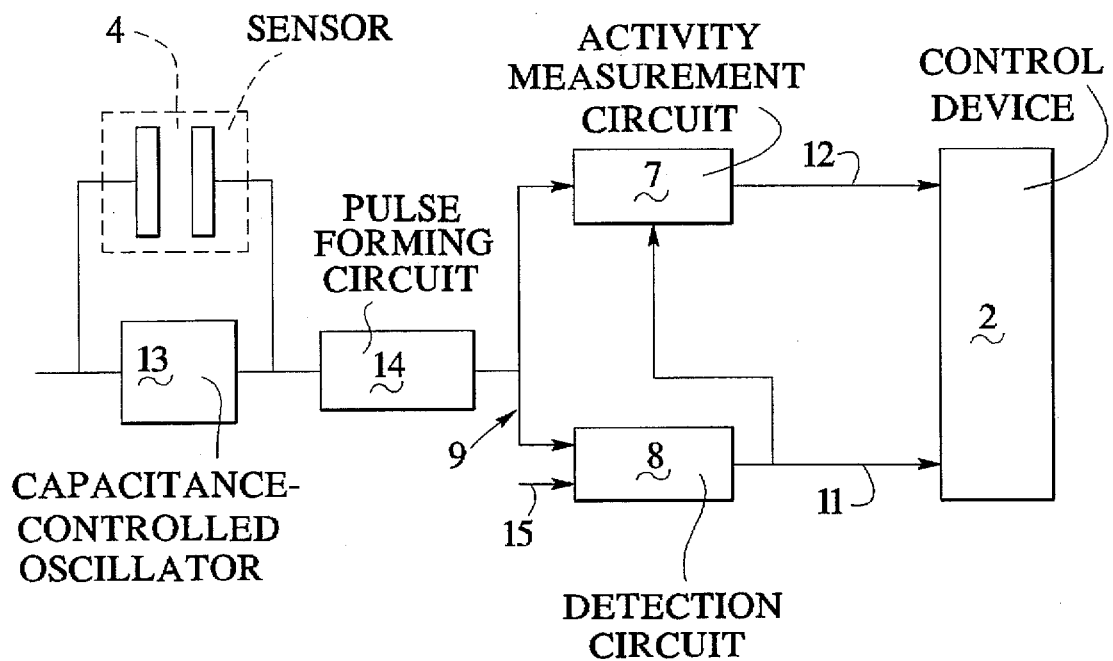
FIG. 4 is a schematic block diagram of a second embodiment of the magnetic field detection portion of the magnetic field/activity detector according to the invention.

FIG. 4 shows the magnetic field detector 3 according to a second embodiment, the magnetic field detector 3 containing a capacitive sensor 4, a capacitance-controlled oscillator 13, a pulse-forming circuit 14, an activity measurement circuit 7 and a detection circuit. Here, the sensor 4 is a capacitive accelerometer 4, which is partially coated with a material sensitive to magnetic fields, just as in the above-described first embodiment. The sensor 4 is connected to the oscillator 13 in such a way that the capacitance of the sensor 4 affects the frequency of the oscillator 13. The oscillator 13 can be, e.g., a conventional RC oscillator in which the frequency is set at several kHz. The output signal of the oscillator 13 is processed in the pulse-forming circuit 14, a measurement signal 9 then being obtained. The pulse-forming circuit 14 consists, e.g., of a Schmitt trigger which straightens the leading and trailing edges so the measurement signal 9 becomes a square wave. The measurement signal 9 is sent to the activation circuit 7 and to the detection circuit 8. In the detection circuit 8, which contains e.g. a counter, the frequency of the measurement signal 9 is compared to an adjustable frequency threshold value 15. If the frequency exceeds this frequency threshold for a predefined period of time, a detection signal 11 is generated and sent to the activity measurement circuit 7 and the control device 2. The predefined period of time is selected in the same way as previously described for the first embodiment.

If the material, sensitive to magnetic fields, with which the sensor 4 has been coated is a permanent magnet material, the absolute change in the frequency of the oscillator 13 is analyzed. This is because the distance between the electrode plates of the sensor 4 either increases or decreases, depending on the polarity of the external magnetic field, causing capacitance to increase or decrease, and causing, in turn, an increase or decrease in the frequency of the oscillator 13.

The threshold 15 is set at a value corresponding to a frequency for the measurement signal 9 when a magnetic field with a predefined strength is present. The change in the frequency of the oscillator 13 in the presence of a magnetic field with a predefined strength is much greater than the changes found in activity measurement. As previously noted, the magnitude of the change can be established during the fabrication of the sensor 4 by varying the thickness of the coating of the electrode plate with a material sensitive to magnetic fields.

The detection signal 11 is therefore generated if a magnetic field with a predefined signal strength is present. In other respects this embodiment operates the same way as the above-described first embodiment.

The magnetic field detector 3 can be used solely for magnetic field detection. Its design is then simpler than the design of the above-described detector, since it does not have any circuits for activity measurement. Two embodiments, solely for magnetic field detection, are described below.

Figure 5:
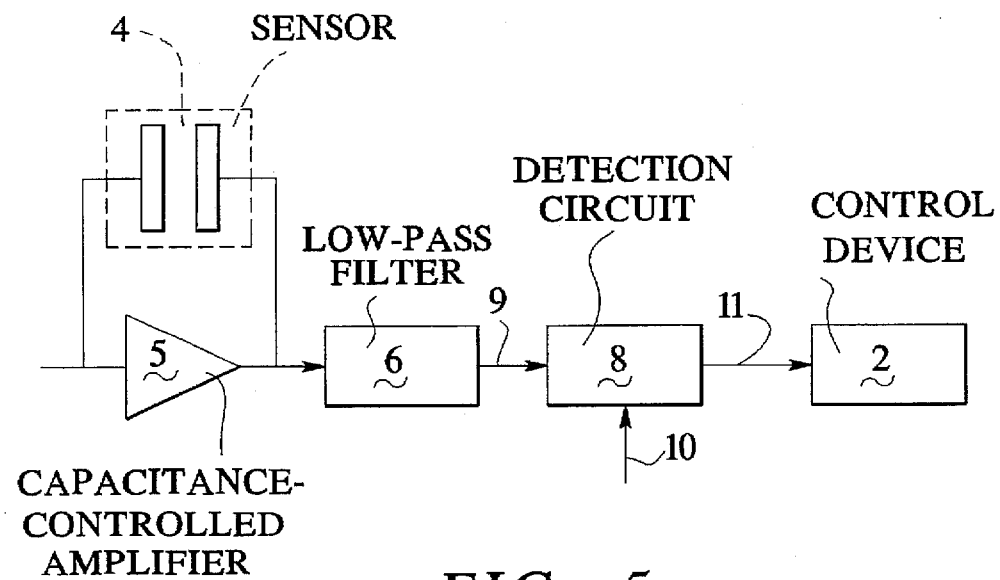
FIG. 5 is a schematic block diagram of a third preferred embodiment of the magnetic field detection portion of the magnetic field/activity detector according to the invention.

FIG. 5 shows a third embodiment of the magnetic field detector 3 which is only used for detection of magnetic fields. The magnetic field detector 3 is connected to a control device 2 and contains a capacitive sensor 4, a capacitance-controlled amplifier 5, a low-pass filter 6 and a detection circuit 8. The sensor 4 is a capacitive accelerometer containing two plates, which are partially coated with a material sensitive to magnetic fields, of the same kind previously described.

The sensor 4 is connected to the amplifier 5 such that the capacitance of the sensor 4 affects the gain of the amplifier 5. The amplifier 5 has a direct current voltage input signal. The output signal of the amplifier 5 is filtered in the low-pass filter 6, thereby producing a measurement signal 9. The measurement signal 9 is supplied to the detection circuit 8. The measurement signal 9 is compared in the detection circuit 8 to an adjustable voltage threshold value 10, whereupon a detection signal 11 is generated and sent to the control device 2 if the measurement signal 9 exceeds this threshold value for a predefined period of time. The voltage threshold 10 is set at a value corresponding to the measurement signal 9 level when a magnetic field with a predefined strength is present. Thus the detection signal 11 is generated when a magnetic field with a predetermined strength is present and sent to the control device 2. The capacitance-controlled amplifier 5 is enabled in the same way as was previously described in conjunction with FIG. 3.

Figure 6:
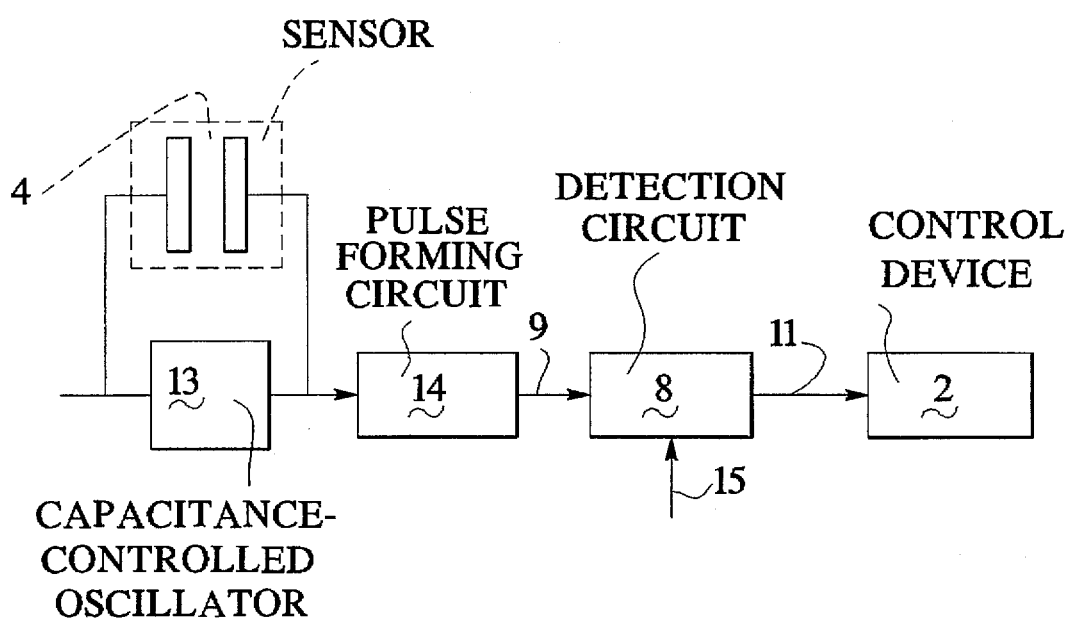
FIG. 6 is a schematic block diagram of a fourth embodiment of the magnetic field detection portion of the magnetic field/activity detector according to the invention.

FIG. 6 shows a fourth embodiment of the magnetic field detector 3 which is only used for the detection of magnetic fields. The magnetic field detector 3 is connected to a control device 2 and contains a capacitive sensor 4, a capacitance-controlled oscillator 13, a pulse-forming circuit 14 and a detection unit 8. Here, the sensor 4 is a capacitive accelerometer, just as in the above-described embodiments, which is partially coated with a material sensitive to magnetic fields. The sensor 4 is connected to the oscillator 13 such that the capacitance of the sensor 4 affects the frequency of the oscillator 13. The oscillator 13 can, e.g., be a conventional RC oscillator in which the frequency is set at several kHz. The output signal of the oscillator 13 is processed in the pulse-forming circuit 14, thereby forming a measurement signal 9. The pulse-forming circuit 14 is e.g., a Schmitt trigger which straightens the leading and trailing so the measurement signal 9 becomes a square wave. The measurement signal 9 is sent to the detection circuit 8. In the detection circuit 8, which contains, e.g., a counter, the frequency of the measurement signal 9 is compared to an adjustable frequency threshold value 15, whereupon a detection signal 11 is generated and sent to the control device 2 if the measurement signal 9 exceeds this threshold value for a predefined period of time. Even in this embodiment, as in the second embodiment, the absolute change in frequency must be analyzed if the sensor 4 has been coated with a permanent magnet material. The threshold 15 is set at a value corresponding to the frequency of the measurement signal 9 when a magnetic field with a predefined strength is present. Thus, the detection signal 11 is generated, when a magnetic field is present, and sent to the control device 2.

Figure 7:
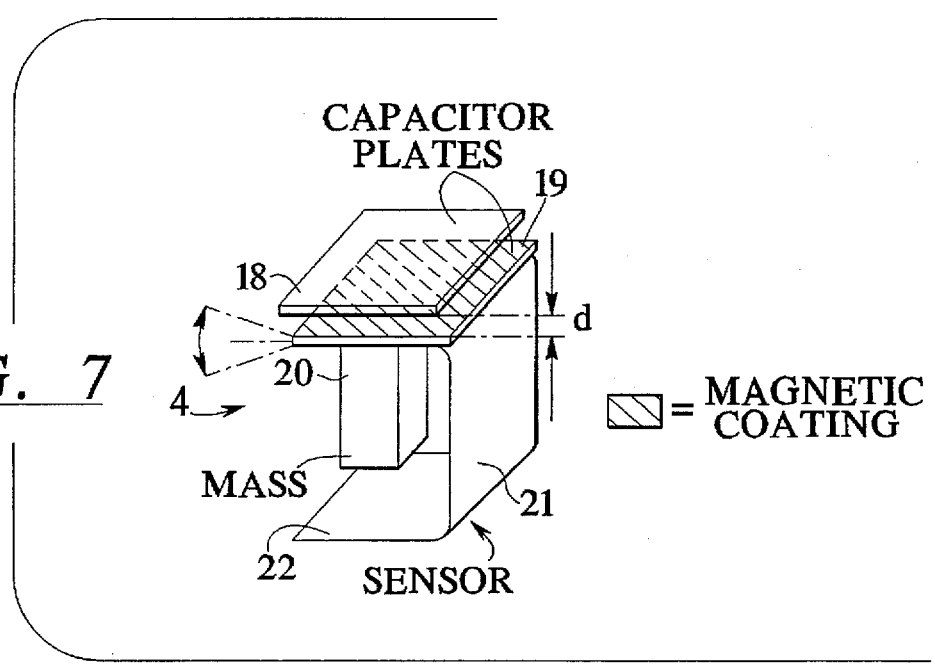
FIG. 7 is a perspective view of an exemplary structural embodiment for the capacitor used in the magnetic field/activity detector according to the invention.

FIG. 7 shows an exemplary structural embodiment of the sensor 4. As noted above, the sensor 4 has a capacitance, this being formed by capacitor plates 18 and 19 with a spacing d therebetween. The capacitor plates 18 and 19 are movable relative to each other; in the embodiment shown in FIG. 7 capacitor plate 18 is stationary and capacitor plate 19 is mounted on one leg of a frame 21, which has an opposite leg 22. A mass 20 is mounted below the capacitor plate 19 on the same leg of the frame 21. The leg 22 is rigidly attached in a suitable manner within the medical implant. Movement (activity) of the patient in whom the medical implant is implanted will thus cause the leg on which the capacitor plate 19 to vibrate or oscillate slightly, facilitated by the mass 20, as indicated by the double arrow in FIG. 7. This movement of the plate 19 changes the capacitance of the capacitor formed by the plates 18 and 19 (and the dielectric, such as air, therebetween) which is used in the aforementioned detection circuits for extracting an activity signal.

The capacitor plate 19 is also shown in FIG. 7 as having the aforementioned magnetic coating thereon, indicated by the slanted lines. This magnetic coating causes the capacitor plate 19 to move in the presence of a magnetic field, thereby also changing the capacitance of the capacitor formed by the plates 18 and 19, as described above.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical implant comprising:
   a capacitive accelerometer having a capacitance which changes upon motion of said capacitive accelerometer and at least partially coated with a material sensitive to magnetic fields which causes a change in the capacitance of said sensor in the presence of a magnetic field;

means connected to said capacitive sensor for generating a signal including a first component dependent on a change in said capacitance due to motion of said capacitive accelerometer and a second component dependent on a change in capacitance of said capacitive accelerometer in the presence of a magnetic field having a predetermined field strength;

means for generating an activity signal dependent on said first component;

means for generating a magnetic field detection signal dependent on said second component;

means for generating a medical therapy, said medical therapy being adjustable and having a plurality of therapy modes;

means connected to said means for generating a medical therapy adapted for delivering said medical therapy to a subject; and control means, supplied with said activity signal and with said magnetic field detection signal, for controlling said means for generating a medical therapy for adjusting said medical therapy dependent on said activity signal and for changing a mode of said medical therapy dependent on said magnetic field detection signal.

2. A medical implant as claimed in claim 1 wherein said means for generating a signal comprises:

a capacitance-controlled unit connected to said capacitive accelerator which emits a measurement signal having at least one measurement signal parameter which changes dependent on the change in capacitance of said capacitive accelerometer; and means connected to said capacitance-controlled unit and supplied with said measurement signal for generating said detection signal if said at least one measurement signal parameter changes to a predetermined value for a predetermined period of time.

3. A medical implant as claimed in claim 2 wherein said capacitance-controlled unit comprises a capacitance-controlled amplifier having a gain, and wherein said at least one measurement signal parameter comprises said gain.

4. A medical implant as claimed in claim 2 wherein said capacitance-controlled unit comprises a capacitance-controlled oscillator having an output frequency, and wherein said at least one measurement signal parameter comprises said output frequency.

5. A medical implant as claimed in claim 1 wherein said capacitive accelerometer comprises at least two electrode plates, moveable relative to each other, and said capacitance of said capacitive accelerometer changing dependent upon a distance between said at least two electrode plates.

6. A medical implant as claimed in claim 5 wherein at least one of said electrode plates is coated with said material sensitive to magnetic fields.

* * * * *